United States Patent
Tanigawa et al.

(10) Patent No.: US 6,482,995 B1
(45) Date of Patent: Nov. 19, 2002

(54) PROCESS FOR PRODUCING AN ALICYCLIC UNSATURATED ALCOHOL

(75) Inventors: Hiroto Tanigawa, Ohtake (JP); Koichi Okumura, Matsudo (JP); Masaya Uenoya, Funabashi (JP); Kango Fujitani, Kyoto (JP); Yoshihiro Kihara, Kyoto (JP)

(73) Assignee: Daicel Chemical Industries, Ltd, Sakai (JP)

( * ) Notice: Subject to any disclaimer, the term of this patent is extended or adjusted under 35 U.S.C. 154(b) by 0 days.

(21) Appl. No.: 10/160,356

(22) Filed: May 30, 2002

(30) Foreign Application Priority Data

May 30, 2001 (JP) .......................................... 2001-163531

(51) Int. Cl.⁷ ............................................... C07C 35/18
(52) U.S. Cl. ........................................................ 568/826
(58) Field of Search ........................................... 568/826

(56) References Cited

U.S. PATENT DOCUMENTS 3,412,042 A * 11/1968 Kudo
5,438,111 A *  8/1995 Panster

* cited by examiner

*Primary Examiner*—Michael L. Shippen
(74) *Attorney, Agent, or Firm*—Morgan & Finnegan, LLP

(57) ABSTRACT

An alicyclic unsaturated alcohol (for example, tetrahydrobenzyl alcohol) having the purity of 99% by weight or more, the water content of 0.1% by weight or less and the acid value of 0.1 mg KOH/g or less can be produced, with high selectivity, by hydrogenating using an unsaturated cyclic aldehyde having the acid value of 10 mg KOH/g or less as a raw material; terminating the hydrogenation in the conversion of 70 to 99.8%; and rectifying the reaction product containing the unreacted unsaturated cyclic aldehyde. The high purity alicyclic unsaturated alcohol is useful as raw material chemicals for synthesizing drugs, agricultural chemicals, perfumes, and dyes etc.

5 Claims, No Drawings

PROCESS FOR PRODUCING AN ALICYCLIC UNSATURATED ALCOHOL

BACKGROUND OF THE INVENTION

1. Field of the Invention

The present invention relates to a process for producing an alicyclic unsaturated alcohol and a high purity tetrahydrobenzyl alcohol. Specifically, the present invention relates to a process for producing an alicyclic unsaturated alcohol used for a great variety of industrial applications, for example, as raw chemicals for synthesizing drugs; agricultural chemicals, perfumes, dyes, etc. more specifically, the present invention relates to a process for producing, with high selectivity, an appropriate alicyclic unsaturated alcohol such as tetrahydrobenzyl alcohol useful as an intermediate raw material for epoxy resins, and the like, and a high purity tetrahydrobenzyl alcohol having a low acid value and a low water content.

2. Description of the Related Art

As a process for producing an alicyclic unsaturated alcohol such as tetrahydrobenzyl alcohol by hydrogenating an unsaturated cyclic aldehyde such as tetrahydrobenzaldehyde, that is, a process for obtaining an alicyclic unsaturated alcohol by selectively reducing a carbonyl moiety in the unsaturated cyclic aldehyde, conventionally, the process for obtaining a corresponding unsaturated alcohol using a reducing reagent, for example, by reducing using lithium aluminum hydride (A. Guiotto. et al., Farmaco. Ed. Sci. 72 (12), 1045–52 (1972)), or by reducing using sodium borohydride (Neth. Appl. 790242 (Sep. 18, 1979)) is known.

The method using $LiAlH_4$, $NaBH_4$, or the like as a reducing reagent is one which is capable of producing, with high-selectivity, the alicyclic unsaturated alcohol, for example, in which the conversion is 98 mol % or more, the selectivity of the desired alicyclic unsaturated alcohol is 97 to 98 mol %, the by-produced alicyclic saturated alcohol is 2 to 3 mol %, and a little saturated cyclic aldehyde is produced. However, the method is very disadvantageous for the industrial applications, since the reducing reagent used is very expensive and a large quantity of the reducing reagent must be used. Also, a large quantity of waste water is generated, because the method requires a large quantity of water for the reaction. Thus, there has been the problem of requiring very high cost for disposing of waste water. Moreover, the method has had the disadvantage in that it is difficult to apply the method to the industrial application because of its economic inferiority. Therefore, the method of synthesizing the alicyclic unsaturated alcohol without using such reducing reagents is sought.

Furthermore, the method of performing a hydrogen migration reaction using tetrahydrobenzaldehyde and alcohols as well as a catalyst is known (JP 63–275538 A).

Although the above-mentioned method can achieve the high selectivity, there is a problem in that the method requires aluminum alcoholate and alcohols of more than equimolar amount of the main raw material and also an equimolar amount of ketones is by-produced.

Therefore, the various methods of hydrogenating using a catalyst have been investigated as the method of synthesizing the alicyclic unsaturated alcohol without using the reducing reagents. For example, the method of hydrogenating using a copper-chromite catalyst, for example, the reaction using a copper-chromite as a catalyst under compression of hydrogen gas (Neth. Appl. 6, 603, 211 (Sep. 13, 1966)) and the reaction using a copper-chromite as a catalyst as well as cyclohexane, tetrahydrofuran as a solvent under compression of hydrogen gas (Ger. 1, 101, 409 (Mar. 9, 1961), J. Falbe. et. al., Chem. Ber. 98 (6), 1928–37 (1965)), and the method of hydrogenating using catalysts carried by Co, Rh-Sn, Ru-Sn, or the like on alumina, silica, zeolite, or the like under compression of hydrogen gas, for example, "The synthesis of crotyl alcohol by selectively hydrogenating crotonaldehyde using an alumina-carried bimetallic catalyst" (Nippon kagaku kaishi (Japanese), 1994 (5), 487–489: SAITAMA UNIVERSITY), and "The selective vapor phase hydrogenation of crotonaldehyde on an Ru-Sn-carried catalyst" (the 76th Catalyst Society of Japan Meetings, 3E15,228 (1995): KOBE UNIVERSITY), are known.

However, the methods using those catalysts are still insufficient for selectivity of the desired unsaturated alcohol, and there is a problem in that the saturated cyclic aldehyde and alicyclic saturated alcohol, which are by-products, are produced in an amount of more than that of the desired product.

As the method of improving the above-mentioned method, the reaction using an alumina-carried cobalt catalyst under compression of hydrogen gas is known (JP 10–236995 A). In the method, the catalyst obtained by adding to the above-mentioned alumina-carried cobalt catalyst containing the second metals (Pt, Ru, Fe, Cu, Rh, etc.) is used to hydrogenate an unsaturated aldehyde using a polar solvent such as an alcohol, and then, the carbonyl moiety in the unsaturated aldehyde having a double bond in the molecule is selectively hydrogenated to selectively produce a corresponding unsaturated alcohol.

However, the hydrogenation according to the above-mentioned method indispensably requires the presence of the polar solvent, and has poor productivity and is not sufficient for the industrial application.

When tetrahydrobenzyl alcohol as the alicyclic unsaturated alcohol is used as an example, impurities at the time of production of the alcohol include tetrahydrobenzaldehyde (3-cyclohexenecarboaldehyde) which is a raw material, and hexahydrobenzyl alcohol, cycrohexanecarboaldehyde, and the like, which are by-products. In general, those impurities are industrially separated by rectification.

The boiling points of the impurities contained in the desired unsaturated alcohol (3-cyclohexenemethanol; boiling point: 183° C.) are 163° C. (for 3-cyclohexenecarboaldehyde), 161° C. (for cyclohexanecarboaldehyde), and 181° C. (for cyclohexanemethanol).

The boiling point of the unsaturated cyclic aldehyde as the raw material which is one of the impurities, is relatively low compared to the alicyclic unsaturated alcohol, and they have the difference of boiling points of from 20 to 30° C. Thus, they can be separated by rectification. However, the boiling point of the alicyclic saturated alcohol which is another by-product, is almost equal to that of the alicyclic unsaturated alcohol. As a result, the industrial-scale separation is substantially impossible, and thus, the by-products, which are difficult to separate, are provided with being contained in the article.

However, when the above-mentioned unsaturated alcohol is used as a perfume, the regulation on the concentration of the saturated alcohol which is an impurity is very strict, and it is pointed out that even the product having the overspeck of 0.1 mol % can not be the article.

Moreover, the alicyclic unsaturated alcohol such as tetrahydrobenzyl alcohol may be used as raw materials for polymers by being subjected to the modification described in the following a) to d), for example.

a) esterifying a hydroxyl group in the alicyclic unsaturated alcohol with an ethylenically unsaturated acid such as acrylic acid and/or methacrylic acid;

b) esterifying a hydroxyl group in the alicyclic unsaturated alcohol with an ethylenically unsaturated acid such as acrylic acid and/or methacrylic acid, and epoxidizing the double bond;

c) converting the double bond in the alicyclic unsaturated alcohol to a hydroxyl group, and esterifying the produced hydroxyl group with the above-mentioned ethylenically unsaturated acid, or the like to form diester or triester; or d) epoxidizing the double bond in the alicyclic unsaturated alcohol, and further converting the hydroxyl group to glycidyl group.

In the above-mentioned case, the low purity due to the remaining alicyclic saturated alcohol as well as saturated and unsaturated aldehyde, and the like causes those impurities to remain as the unreacted components in polymerization, and thus it is not preferable.

Furthermore, much water content inhibits the reaction when the double bond is epoxidized, which is very not preferable.

Moreover, the free carboxylic acids which contribute to acid value have a different odor from that of the desired product and they are the reactive impurities, thus it is not preferable to contain the free acids in any way. Therefore, the reduction of the free acids is required.

SUMMARY OF THE INVENTION

In view of the above-mentioned problems, it is required that an alicyclic unsaturated alcohol which is a final product has high purity. Thus, an object of the present invention is to provide a process for producing, with high-selectivity, a high purity alicyclic unsaturated alcohol having a purity of 99% by weight or more, a water content of 0.1% by weight or less and an acid value of 0.1 mg KOH/g or less.

To achieve the above object, the present inventors have intensely studied hydrogenation of an unsaturated cyclic aldehyde in the presence of a catalyst. As a result, the inventors have found that although the alicyclic unsaturated alcohol is usually produced in an early stage of the reaction under the condition of using the selected catalyst useful for the present invention, the produced alicyclic unsaturated alcohol is converted to the further hydrogenated alicyclic saturated alcohol in a later stage of the reaction. Also, the inventors have found that it is very important that the by-production of the alicyclic saturated alcohol is controlled as significantly as possible, since the separation of the alicyclic saturated alcohol is very difficult as described above. Therefore, the inventors have found that it can be extremely important that the hydrogenation is terminated before the alicyclic saturated alcohol is produced, and that the unreacted unsaturated cyclic aldehyde is cut in a separation step such as rectification.

Moreover, the inventors have confirmed that a copper-chromite catalyst has particularly high ability for the selective hydrogenation of a carbonyl moiety in the reduction of the unsaturated cyclic aldehyde and the hydrogenation of the double bond, and have found that the hydrogenation is terminated in a stage with a strictly controlled degree of reaction by strictly controlling the reaction condition, thereby inhibiting or inactivating the hydrogenation of the double bond to obtain the desired alicyclic unsaturated alcohol with the high selectivity and the high yield. As a result, a composition, which it is easy to separate by rectification, is provided, and the high purity alicyclic unsaturated alcohol with the high yield is produced. Thus, the present invention has been completed.

According to a first aspect of the present invention, there is provided a process for producing an alicyclic unsaturated alcohol having the purity of 99% by weight or more, the water content of 0.1% by weight or less and the acid value of 0.1 mg KOH/g or less, characterized by comprising:

(1) hydrogenating using an unsaturated cyclic aldehyde having the acid value of 10 mg KOH/g or less as a raw material;

(2) terminating the hydrogenation in the conversion of 70 to 99.8%; and (3) rectifying a reaction product containing the unreacted unsaturated cyclic aldehyde;

in the production of an alicyclic unsaturated alcohol by hydrogenating the unsaturated cyclic aldehyde represented by the following general formula (1)

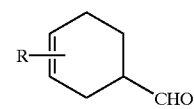

(1)

wherein R represents a hydrogen or a methyl group, in the presence of a catalyst.

According to a second aspect of the present invention, there is provided a process for producing a tetrahydrobenzyl alcohol having the purity of 99% by weight or more, the water content of 0.1% by weight or less and the acid value of 0.1 mg KOH/g or less, characterized by comprising:

(1) hydrogenating using a tetrahydrobenzaldehyde having the acid value of 10 mg KOH/g or less as a raw material;

(2) terminating the hydrogenation in the conversion of 70 to 99.8%; and (3) rectifying a reaction product containing the unreacted tetrahydrobenzaldehyde; in the production of tetrahydrobenzyl alcohol by hydrogenating tetrahydrobenzaldehyde in the presence of a catalyst.

According to a third aspect of the present invention, in the first or second aspect of the present invention, there is provided a method, characterized in that the catalyst used is copper, copper-zinc, copper-chromium, copper-zinc-chromium or one or more mixed catalysts selected from the oxides thereof, or a modified product thereof with molybdenum, tungsten, magnesium, barium, aluminum, calcium, zirconium, manganese, nickel or the oxides thereof.

According to a fourth aspect of the present invention, in a first or second aspect of the present invention, there is provided a method, characterized in that the hydrogenation is performed under pressure of hydrogen gas of 0.1 to 8 MPa.

According to a fifth aspect of the present invention, there is provided a tetrahydrobenzyl alcohol having the purity of 99% by weight or more, the water content of 0.1% by the weight or less and the acid value of 0.1 mg KOH/g or less, obtained by using the method according to the second aspect of the present invention.

DETAILED DESCRIPTION OF THE INVENTION

The alicyclic unsaturated alcohol obtained by the production method according to the present invention is used as raw materials for drugs, agricultural chemicals, perfumes, dyes, monomers for polymers, and the like.

The present invention is a process for producing an alicyclic unsaturated alcohol having the purity of 99% by weight or more, the water content of 0.1% by weight or less and the acid value of 0.1 mg KOH/g or less, characterized by comprising:

(1) hydrogenating using an unsaturated cyclic aldehyde having the acid value of 10 mg KOH/g or less as raw material;

(2) terminating the hydrogenation in the conversion of 70 to 99. 8%, preferably 80 to 99. 8%, more preferably 90 to 99. 8% ; and (3) rectifying a reaction product containing the unreacted unsaturated cyclic aldehyde;

in the production of the alicyclic unsaturated alcohol by hydrogenating the unsaturated cyclic aldehyde represented by the following general formula (1)

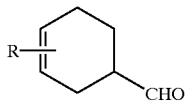

(1)

wherein R represents a hydrogen or a methyl group, in the presence of a catalyst.

The unsaturated cyclic aldehyde used for the present invention may be synthesized or naturally occurring products. In the case of the synthesized aldehyde, tetrahydrobenzaldehyde (3-cyclohexenecarboaldehyde, in other words, 1, 2, 3, 6 - tetrahydrobenzaldehyde), which i s represented by the formula (1) wherein R is a hydrogen, is used in many cases because of the easy availability of the raw material.

The acid value of the raw material is 10 mg KOH/g or less, preferably 1 mg KOH/g or less.

The acid value of the raw material of more than 10 mg KOH/causes the copper component in the catalyst to elute at the hydrogenation step to deteriorate the catalyst. Moreover, the various problems are caused that the eluted copper is reduced with hydrogen gas and is re-deposited inside the reaction tube to form the mirror-like metal coating, or the eluted copper forms the metal coating reduced with the remaining aldehyde on the bottom of the distilling column, and the like. When the acid value of the raw material is more than 10 mg KOH/g, the acid value of the obtained alicyclic unsaturated alcohol becomes greater even though the conversion is controlled within the range of 70 to 99.8%. Thus, this is not preferable for raw materials for synthesizing drugs, agricultural chemicals, perfumes, dyes etc.

Also, since the free carboxylic acid exists greatly after the hydrogenation step, the operation of continuing to rectify tetrahydrobenzyl alcohol which is a main fraction in the state of high reflux ratio is required so as not to distill the free carboxylic acid in the rectification step. Thus, the productivity is remarkably reduced.

The examples of the catalyst used for the present invention include copper, copper-zinc, copper-chromium, copper-zinc-chromium or one or more mixed catalysts selected from the oxides thereof, or modified products thereof with molybdenum, tungsten, magnesium, barium, aluminum, calcium, zirconium, manganese, nickel or the oxides thereof.

Specific examples of preferred catalysts include copper-chromium oxide, copper-zinc oxide, copper-zinc-chromium oxide, copper-chromium-magnesium oxide, copper-chromium-barium oxide, copper-chromium-manganese oxide, copper-chromium-magnesium-manganese oxide, copper-chromium-magnesium-barium oxide, copper-chromium-manganese-barium oxide, copper-chromium-magnesium-manganese-barium oxide, copper-zinc-aluminum oxide, copper-zinc-magnesium oxide, copper-zinc-barium oxide, copper-zinc-manganese oxide, copper-zinc-magnesium-manganese oxide, copper-zinc-magnesium-barium oxide, copper-zinc-manganese-barium oxide, copper-zinc-magnesium-manganese-barium oxide. As those catalysts, the commercially available catalysts such as N203, N203S, N203SD, N203SDB (manufactured by Nikki Chemical Co., Ltd.), Cu-0202P, Cu-1106P, Cu-1160P, Cu-1800P, Cu-1850P, Cu-1950P, Cu-0891P manufactured by N.E Chemcat Corp.), and CB-2, C-5A, C-100, C-700, C-900 (manufactured by Sakai Chemical Industries, Ltd.) can be used.

Moreover, in addition to the above-mentioned metal and metal oxides, the catalysts, which are, added with the formation aids such as diatomaceous earth (kieselguhr), clay and graphite, or the carried catalysts of the above-mentioned metal oxide on the carrier such as alumina and silica can be used.

Those catalysts can be used as they are. Also, a suitable activating process such as the reduction process prior to use of the catalyst is preferably performed.

The amount used of those catalysts is 0.001% weight or more, preferably 0.1 to 10% by weight with respect to the unsaturated cyclic aldehyde which is a starting material. When the usage of the catalyst is 0.001% by weight or less, it is impractical since the reaction rate is very slow. To the contrary, when the catalyst of 10% by weight or more is used, it is not economical since the reaction rate is not improved.

The hydrogenation according to the present invention may be any of a batch process, a semi-batch process or a continuous process. A mixing tank, a tubular type reactor, or the like can be used as a reactor.

The above-mentioned catalyst is usually in a solid state or powdery. When the method for the production is a batch process, the solid-state or powdery catalyst is introduced into the reactor charged with the unsaturated cyclic aldehyde, and the reactor is replaced with an inert gas such as nitrogen gas, and is then filled with hydrogen gas. Thus the hydrogenation is carried out.

When the method is a continuous process, the unsaturated cyclic aldehyde is mixed with the catalyst in a premixing tank, and the mixture is continuously entered into the reactor for hydrogenation. Thus the reaction is carried out.

When a fixed bed reactor is used, a tablet type solid catalyst is charged into a tubular type reactor to use.

The production process according to the present invention does not particularly require a solvent, but, a solvent may be optionally used. The solvents selected are not particularly limited as long as the solvents are inactive to the reaction, and can dissolve the raw material and the alicyclic unsaturated alcohol which is a reaction product and also can be separated by rectification. As the solvent, a primary alcohol having 2 to 6 carbon atoms, ethers, and like are selected.

The reaction temperature for the hydrogenation according to the present invention is not particularly limited, but, too high reaction temperature causes low selectivity and produces quantities of saturated alcohol which can not be separated. As a result, the saturated alcohol remains in a final product, and thus the industrial purity can not be satisfied. Moreover, too high temperature causes the dehydration to increase water content in the reaction product. Thus, the hydrogenation is preferably performed at 30 to 200° C., more preferably 100 to 180° C.

The pressure for the hydrogenation according to the present invention is desirably within the range of 0.1 to 8 MPa, more preferably 0.5 to 5 MPa. When the pressure in the hydrogenation is too low, the reaction can not proceed. To the contrary, too high pressure is not preferred because the selectivity between the reduction of the aldehyde and the hydrogenation of the double bond is reduced.

The hydrogenation is terminated in the conversion of 70 to 99.8%. Terminating the reaction in the conversion of 70 to 99.8%, preferably 80 to 99.8%, more preferably 90 to 99.8% can achieve the required selectivity in the reaction and the productivity. When the reaction is terminated in the conversion of lower than 70%, the productivity is reduced, and when the conversion is greater than 99.8%, a quantity of cyclohexylalcohol which is an unnecessary product by the excess reaction is produced, which is not preferred. The termination point in the hydrogenation can be determined by analyzing the remaining unsaturated cyclic aldehyde in the reaction system.

After the hydrogenation is completed, the impurities are separated by rectification. A rectifying column having the theoretical plate number of 5 to 30 plate numbers is sufficient to separate, and preferably, a rectifying column having the theoretical plate number of 10 to 25 plate numbers is used to separate. In general, a rectifying column having the theoretical plate number of 20 plate numbers is used. The rectifying temperature and the degree of the reduced pressure vary depending on the alicyclic unsaturated alcohol and the impurities, but in the case of tetrahydrobenzyl alcohol, the rectification is preferably carried out under the condition of the temperature at the column top of 80 to 200° C. and the degree of the reduced pressure of 10 to 300 mmHg;

The thus obtained alicyclic unsaturated alcohol has the purity of 99% by weight or more, the water content of 0.1% by weight or less and the acid value of 0.1 mg KOH/g or less, preferably 0.05 mg KOH/g or less.

EXAMPLES

The present invention will be illustrated in detail by the following examples, but the present invention is not limited by the examples. As for the following "catalyst", the commercially available product itself was conveniently used. The method for the analysis was as described below. Gas chromatographic analysis Column: DB-5 (capillary column); 30 m; inner diameter: 0.53 mm; thickness: 1.5 micron Dodecane was used as an internal standard substance, and the weight percentage of each component was calculated from the area ratio of each component to the internal standard substance.

Water content: Karl Fischer technique (% by weight)

Acid value: basic analysis method for oils&fats (mg KOH/g)

Example 1

50 g of tetrahydrobenzaldehyde (3-cyclohexenecarboaldehyde; purity: 99.7% by weight; 0.5 mg KOH/g) and 0.5 g of copper-chromite catalyst C-700 (manganese/magnesium-modified copper-chromite) manufactured by Sakai Chemical Industries, Ltd. were introduced into an autoclave made of stainless steel, which was equipped with a stirrer, a thermometer and a pressure gauge, and the autoclave was replaced with nitrogen and then filled with hydrogen. The hydrogenation was performed at the temperature of 150° C. under the pressure of 3 MPa for 9 hours, and the reaction was terminated in the conversion of 98.1% by purging hydrogen (there action termination point was determined based on the amount of the remaining tetrabenzaldehyde by gas chromatography analysis (The same method was also used in the following Examples).

The composition of a crude reaction product by gas chromatography analysis was 97.6% by weight of tetrahydrobenzyl alcohol which is a target product, 1.9% by weight of tetrahydrobenzaldehyde which is a raw material, 0.2% by weight of hexahydrobenzyl alcohol and 0.3% by weight of unidentified components.

The crude reaction product was placed into a laboratory rectifying column having the theoretical plate number of 10 plate numbers, and the rectification was carried out under the condition of the temperature at the column top of 96 to 109° C., the degree of the reduced pressure of 23 to 44 mmHg and the reflux ratio of 1 to obtain 46. 5 g of a rectified product of tetrahydrobenzyl alcohol (3-cyclohexenemethanol) (yield: 91.3%). It was shown by the analysis that the rectified product had the water content of 0.02% by weight, the acid value of 0.01 mg KOH/g, and the purity by the gas chromatography analysis of 99.6% by weight.

Example 2

The hydrogenation was performed by the same method as in the Example 1 except that the copper-chromite catalyst was substituted for 1850P (copper-chromite) manufactured by N.E. Chemcat Corp. The reaction was terminated in the conversion of reaction of 98% by purging hydrogen. The composition of a crude reaction product by gas chromatography analysis was 97.4% by weight of tetrahydrobenzyl alcohol which is a target product, 2.0% by weight of tetrahydrobenzaldehyde which is a raw material, 0.3% by weight of hexahydrobenzyl alcohol and 0.3% by weight of unidentified components.

The rectification was carried out by the same method as in the Example 1 to obtain 47.6 g of a rectified product (yield: 93.5%). It was shown by the analysis that the rectified product had the water content of 0.03% by weight, the acid value of 0.01 mg KOH/, and the purity by the gas chromatography analysis of 99.3% by weight.

Example 3

The hydrogenation was performed by the same method as in the Example 1 except that the copper-chromite catalyst was substituted for N-203 (manganese-modified copper-chromite) manufactured by Nikki Chemical Co., Ltd. The reaction was terminated in the conversion of 96% by purging hydrogen. The composition of a crude reaction product by gas chromatography analysis was 95.4% by weight of tetrahydrobenzyl alcohol which is a target product, 4.0% by weight of tetrahydrobenzaldehyde which is a raw material, 0.3% by weight of hexahydrobenzyl alcohol and 0.3% by weight of unidentified components.

The rectification was carried out by the same method as in the Example 1 to obtain 46.2 g of a rectified product (yield: 90.8%). It was shown by the analysis that the rectified product had the water content of 0.02% by weight, the acid value of 0.01 mg KOH/g, and the purity by the gas chromatography analysis of 99.4% by weight.

Example 4

The hydrogenation was performed by the same method as in the Example 1 except that the reaction was terminated in the conversion of 85.0%.

The composition of a crude reaction product by gas chromatography analysis was 84.5% by weight of tetrahydrobenzyl alcohol which is a target product, 15.0% by weight of tetrahydrobenzaldehyde which is a raw material, 0.2% by weight of hexahydrobenzyl alcohol and 0.3% by weight of unidentified components.

The rectification was carried out by the same method as in the Example 1 to obtain 38.9 g of a rectified product (yield: 76.4%). It was shown by the analysis that the rectified product had the water content of 0.02% by weight, the acid value of 0.01 mg KOH/g, and the purity by the gas chromatography analysis of 99.1% by weight.

Example 5

The hydrogenation was performed by the same method as in the Example 1 except that the reaction was terminated in the conversion of 99.8%. The composition of a crude reaction product by gas chromatography analysis was 99.1% by weight of tetrahydrobenzyl alcohol which is a target product, 0.2% by weight of tetrahydrobenzaldehyde which is a raw material, 0.7% by weight of hexahydrobenzyl alcohol and 0.3% by weight of unidentified components.

The rectification was carried out by the same method as in the Example 1 to obtain 45.7 g of a rectified product (yield: 89.8%). It was shown by the analysis that the rectified product had the water content of 0.02% by weight, the acid value of 0.01 mg KOH/g, and the purity by the gas chromatography analysis of 99.1% by weight.

Example 6

The hydrogenation was performed by the same method as in the Example 1 except that a tetrahydrobenzyl alcohol having the purity of 99.7% by weight and acid value of 3 mg KOH/g was used. The composition of a crude reaction product by gas chromatography analysis was 97.4% by weight of tetrahydrobenzyl alcohol which is a target product, 1.9% by weight of tetrahydrobenzaldehyde which is a raw material, 0.2% by weight of hexahydrobenzyl alcohol and 0.5% by weight of unidentified components.

The rectification was carried out by the same method as in the Example 1 to obtain 45.6 g of a rectified product (yield: 91.2%). It was shown by the analysis that the rectified product had the water content of 0. 04% by weight, the acid value of 0.06 mg KOH/g, and the purity by the gas chromatography analysis of 99.5% by weight.

Example 7

The hydrogenation was performed by the same method as in the Example 1 except that a tetrahydrobenzyl alcohol having the purity of 99.7% by weight and acid value of 8mgKOH/g was used. The composition of a crude reaction product by gas chromatography analysis was 97.5% by weight of tetrahydrobenzyl alcohol which is a target product, 1.9% by weight of tetrahydrobenzaldehyde which is a raw material, 0.2% by weight of hexahydrobenzyl alcohol and 0.4% by weight of unidentified components.

The rectification was carried out by the same method as in the Example 1 to obtain 45.0 g of a rectified product (yield: 90. 0%). It was shown by the analysis that the rectified product had the water content of 0.06% by weight, the acid value of 0.08 mg KOH/g, and the purity by the gas chromatography analysis of 99.3% by weight.

Comparative Example 1

The hydrogenation was performed by the same method as in the Example 1 except that the reaction was terminated in the conversion of 67.5%.

The composition of a crude reaction product by gas chromatography analysis was 66.0% by weight of tetrahydrobenzyl alcohol which is a target product, 33.5% by weight of tetrahydrobenzaldehyde which is a raw material, 0.2% by weight of hexahydrobenzyl alcohol and 0.3% by weight of unidentified components.

Then the rectification was carried out by the same method as in the Example 1 to obtain 26.8 g of a rectified product of tetrahydrobenzyl alcohol (3-cyclohexenemethanol) (yield: 52.6%). It was shown by the analysis that the rectified product had the water content of 0.02% by weight, the acid value of 0.01 mg KOH/g, and the purity by the gas chromatography analysis of 98.6% by weight.

Comparative Example 2

The hydrogenation was performed by the same method as in the Example 1 except that the reaction was terminated in the degree of reaction of 99.95%. The composition of a crude reaction product by gas chromatography analysis was 94.8% by weight of tetrahydrobenzyl alcohol which is a target product, 0.1% by weight of tetrahydrobenzaldehyde which is a raw material, 5.0% by weight of hexahydrobenzyl alcohol and 0.1% by weight of unidentified components.

Then the rectification was carried out by the same method as in the Example 1 to obtain 45.0 g of a rectified product (yield: 88.4%). It was shown by the analysis that the rectified product had the water content of 0.02% by weight, the acid value of 0.01 mg KOH/g, and the purity by the gas chromatography analysis of 94.8% by weight. The rectified product contained 5.0% by weight of hexahydrobenzyl alcohol.

Comparative Example 3

The hydrogenation was performed by the same method as in the Example 1 except that the acid value of the raw material was 11.0 mg KOH/g. The reaction was terminated in the conversion of 98.1% by purging hydrogen. The composition of a crude reaction product by gas chromatography analysis was 97.6% by weight of tetrahydrobenzyl alcohol which is a target product, 1.9% by weight of tetrahydrobenzaldehyde which is a raw material, 0.2% by weight of hexahydrobenzyl alcohol and 0.3% by weight of unidentified components.

Then the rectification was carried out by the same method as in the Example 1 to obtain 46.4 g of a rectified product (yield: 91.1%). It was shown by the analysis that the rectified product had the water content of 0.02% by weight, the acid value of 0.5 mg KOH/g, and the purity by the gas chromatography analysis of 99.5% by weight. The considerable deposition of the metal derived from the catalyst was observed inside the autoclave and in the bottom of the distillation column.

According to the production process of the present invention, the alicyclic unsaturated alcohol having the high purity, low water content and low acid value can be produced with high selectivity and high yield.

What is claimed is:

1. A process for producing an alicyclic unsaturated alcohol having the purity of 99% by weight or more, the water content of 0.1% by weight or less and the acid value of 0.1 mg KOH/g or less, the process comprising:
   (1) hydrogenating using an unsaturated cyclic aldehyde having the acid value of 10 mg KOH/g or less as a raw material;
   (2) terminating the hydrogenation in the conversion of 70 to 99.8%; and (3) rectifying a reaction product containing the unreacted unsaturated cyclic aldehyde;

in the production of the alicyclic unsaturated alcohol by hydrogenating the unsaturated cyclic aldehyde represented by the following general formula (1):

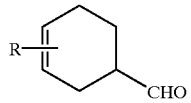 (1)

wherein R represents a hydrogen or a methyl group, in the presence of a catalyst.

2. A process for producing a tetrahydrobenzyl alcohol having the purity of 99% by weight or more, the water content of 0.1% by weight or less and the acid value of 0.1 mg KOH/g or less, the process comprising:
  (1) hydrogenating using tetrahydrobenzaldehyde having the acid value of 10 mg KOH/g or less as a raw material;
  (2) terminating the hydrogenation in the conversion of 70 to 99.8%; and
  (3) rectifying a reaction product containing the unreacted tetrahydrobenzaldehyde;
    in the production of the tetrahydrobenzyl alcohol by hydrogenating tetrahydrobenzaldehyde in the presence of a catalyst.

3. A method according to claim 1 or 2, wherein the catalyst used is copper, copper-zinc, copper-chromium, copper-zinc-chromium or one or more mixed catalysts selected from the oxides thereof, or a modified catalyst thereof with molybdenum, tungsten, magnesium, barium, aluminum, calcium, zirconium, manganese, and nickel or the oxides thereof.

4. A method according to claim 1 or 2, wherein the hydrogenation is performed under pressure of hydrogen gas of 0.1 to 8 MPa.

5. A tetrahydrobenzyl alcohol having the purity of 99.0% by weight or more, the water content of 0.1% by weight or less and the acid value of 0.1 mg KOH/g or less obtained by using the producing method according to claim 2.

* * * * *